United States Patent
Muñoz Camargo et al.

(10) Patent No.: US 12,194,193 B2
(45) Date of Patent: Jan. 14, 2025

(54) EXTRUDABLE PHOTOCROSSLINKABLE HYDROGEL AND METHOD FOR ITS PREPARATION

(71) Applicant: UNIVERSIDAD DE LOS ANDES, Bogotá (CO)

(72) Inventors: Carolina Muñoz Camargo, Bogotá (CO); Juan Carlos Cruz Jiménez, Bogotá (CO); Julián Andrés Serna Méndez, Bogotá (CO); Laura Rueda Gensini, Bogotá (CO); Javier Felipe Cifuentes Rueda, Bogotá (CO); Daniela Natalia Céspedes Valenzuela, Bogotá (CO)

(73) Assignee: UNIVERSIDAD DE LOS ANDES, Bigota (CO)

( * ) Notice: Subject to any disclaimer, the term of this patent is extended or adjusted under 35 U.S.C. 154(b) by 0 days.

(21) Appl. No.: 18/438,591

(22) Filed: Feb. 12, 2024

(65) Prior Publication Data
US 2024/0181133 A1 Jun. 6, 2024

Related U.S. Application Data

(62) Division of application No. 16/992,708, filed on Aug. 13, 2020, now Pat. No. 11,918,703.

(51) Int. Cl.
| | | |
|---|---|---|
| A61L 27/36 | (2006.01) | |
| A61K 38/17 | (2006.01) | |
| A61L 27/20 | (2006.01) | |
| A61L 27/52 | (2006.01) | |
| A61L 27/54 | (2006.01) | |
| B33Y 40/10 | (2020.01) | |
| B33Y 70/00 | (2020.01) | |
| B29C 64/106 | (2017.01) | |
| B33Y 10/00 | (2015.01) | |

(52) U.S. Cl.
CPC ......... *A61L 27/3633* (2013.01); *A61K 38/17* (2013.01); *A61L 27/20* (2013.01); *A61L 27/3687* (2013.01); *A61L 27/52* (2013.01); *A61L 27/54* (2013.01); *B33Y 40/10* (2020.01); *B33Y 70/00* (2014.12); *A61L 2300/252* (2013.01); *A61L 2300/404* (2013.01); *A61L 2430/00* (2013.01); *B29C 64/106* (2017.08); *B33Y 10/00* (2014.12)

(58) Field of Classification Search
None
See application file for complete search history.

(56) References Cited

U.S. PATENT DOCUMENTS

2019/0022280 A1* 1/2019 Khademhosseini .... A61P 27/02

* cited by examiner

*Primary Examiner* — Nannette Holloman
(74) *Attorney, Agent, or Firm* — The Morales Law Firm; Joseph L. Morales, Esq.

(57) ABSTRACT

The present invention relates to an extrudable photocrosslinkable hydrogel comprising a biochemically modified extracellular matrix (ECM) with an electroconductive nanomaterial embedded; a photoinitiator and a solvent, the method for its preparation starting from decellularized extracellular matrices (dECMs) and its applications for preparing electroconductive scaffolds, electroconductive extrudable hydrogels for in situ defect-filling, conductive grafts, in situ or in vitro printed tissues or organs, adhesives for different tissues, or bone adhesives.

6 Claims, 11 Drawing Sheets

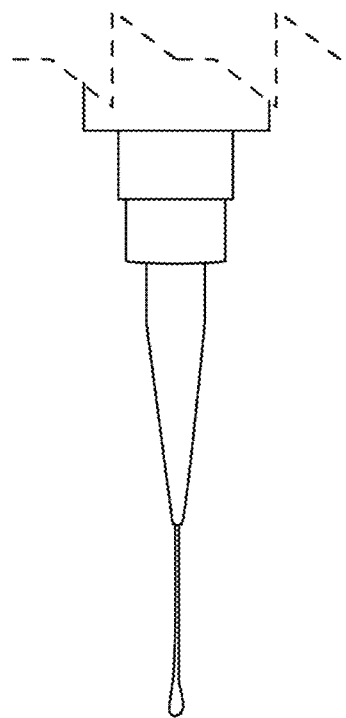
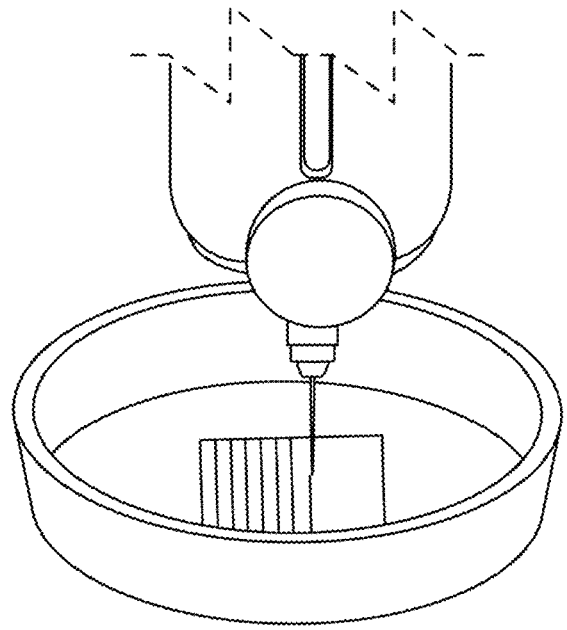
FIG. 8A
FIG. 8B
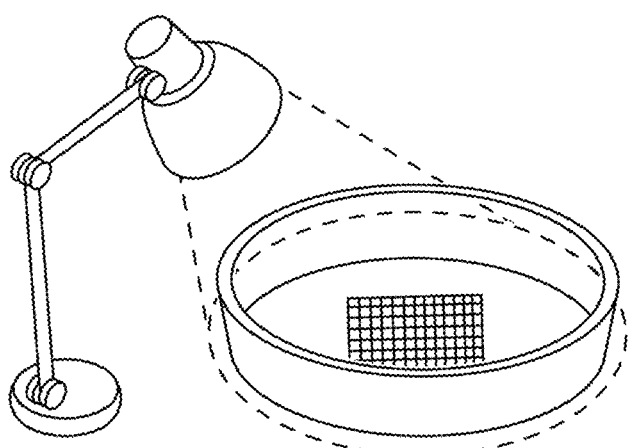
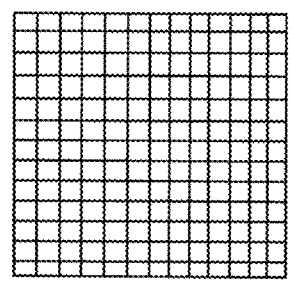
FIG. 8C
FIG. 8D

EXTRUDABLE PHOTOCROSSLINKABLE HYDROGEL AND METHOD FOR ITS PREPARATION

CROSS REFERENCE TO RELATED APPLICATIONS

This application is a divisional application claiming priority from application Ser. No. 16/992,708 filed on Aug. 13, 2020, which is herby incorporated by reference in its entirety.

FIELD OF THE INVENTION

The present invention relates to the field of tissue engineering and biomaterials, particularly to biomaterials suitable for 3D bioprinting. In particular, the present invention relates to an extrudable photocrosslinkable hydrogel comprising a biochemically modified extracellular matrix (ECM) with an electroconductive nanomaterial embedded; a photoinitiator and a solvent; a method for its preparation from decellularized extracellular matrices (dECMs); and its applications.

BACKGROUND OF THE INVENTION 3D bioprinting is rapidly emerging as a powerful tool to aid the development of novel regenerative biomaterials as it provides a route for the fabrication of customized and multifunctional constructs for regeneration of different tissues and organs. In this emerging technology, decellularized extracellular matrices (dECMs) represent a promising alternative as a source of materials for the development of scaffolds that closely mimic the native environment of cells in tissues. As a result, they can then be used to prepare bioinks with the biomimicry attributes required for regeneration purposes.

However, formulating bioinks is still a challenging task due to difficulties in assuring that the printed materials exhibit the mechanical properties of the tissue to be regenerated. Several strategies have been developed over the years for addressing this issue, including crosslinking methods, the addition of synthetic materials as excipients, and the use of synthetic matrices for casting.

For example, WO2018/071639 discloses bioinks made of collagen which can be mixed with cells at neutral pH, and then printed into cell culture media. Collagen may be modified to introduce pendant chemical groups that allow crosslinking under non-toxic conditions for cells with the aid of a crosslinking agent. Furthermore, collagen may be crosslinked without chemical modification or may be crosslinked with a photoinitiator and light exposure.

Similarly, WO2016/019078 refers to biologically-based ink compositions, as well as articles and/or devices that are engineered and fabricated from such compositions. In certain embodiments, bio-ink compositions are self-curing and, in other embodiments, bio-ink compositions upon printing, cure to form a crystallized layer that is substantially insoluble in water. The described bio-ink compositions exhibit mechanical and/or chemical features that are suitable for use as 3D-printable inks.

WO2017/223297 relates to an engineered porous cartilage template having a bone-mimicking internal structure and a method of preparing such porous cartilage template for bone repair. The method comprises 3D-printing a porous network based on bone imaging data followed by casting a cell-carrier component comprising a multitude of cells into the different types of pores in the material, and finally culturing the different types of cells to form mature cartilage, thereby forming the porous cartilage template.

Finally, Serna et al (Formulation and Characterization of a SIS-Based Photocrosslinkable Bioink. Polymers 2019, 11, 569) studied the use of a small intestinal submucosa (SIS) dECM for the manufacture of a bioink with rheological and mechanical properties suitable for extrusion-based 3D bioprinting. Photocrosslinking reactions were carried out in an attempt to control gelation and mechanical properties of the extruded material. As photocrosslinking reactions failed to promote a substantial increase in gelation, authors concluded that there was still a need for strategies to improve the efficiency of photocrosslinking processes and future studies directed towards assessing the role of temperature-induced gelation in the rheological properties of the bioink.

In spite of the strategies that have been attempted for obtaining materials capable of mimicking extracellular environments, processes required for producing such materials, for example UV curing and/or crosslinking, can damage structures and inhibit incorporation of therapeutic molecules and/or cells and ultimately limit applicability under physiological conditions. Moreover, the obtained materials fail to reproduce the extracellular environment needed to regenerate tissues or they do not have properties such as structural integrity needed for bioprinting. In the absence of such properties, these printing strategies are largely constrained to application in in vitro models. Consequently, there still persists the need for biomaterials that address the required rheological properties, mechanical and structural stability needed for extrusion-based 3D bioprinting such that the obtained products are suitable for cell growth.

BRIEF SUMMARY OF THE INVENTION

The present invention relates to an extrudable photocrosslinkable hydrogel comprising a biochemically-modified extracellular matrix (ECM) with an electroconductive nanomaterial embedded; a photoinitiator and a solvent; a method for its preparation starting from decellularized extracellular matrices (dECMs); and its applications.

In a first aspect, the invention refers to a hydrogel comprising a biochemically-modified extracellular matrix (ECM) with an electroconductive nanomaterial embedded; a photoinitiator and a solvent.

In a second aspect, the invention relates to the use of the hydrogel for preparing electroconductive scaffolds, electroconductive extrudable hydrogels for in situ defect-filling, conductive grafts, in situ or in vitro printed tissues or organs, adhesives for different tissues, or bone adhesives.

In a third aspect, the invention refers to a method for preparing an extrudable photocrosslinkable hydrogel comprising biochemically modifying a ECM pregel and its treatment with a working solution comprising a photoinitiator and an electroconductive nanomaterial.

BRIEF DESCRIPTION OF THE DRAWINGS

FIG. 8A Bioprinting process—The methacryloyl-modified ECM hydrogel forms a filament upon extrusion.

FIG. 8B Bioprinting process—Bioprinting process. (C) The bioprinted constructs being irradiated with visible light after extrusion to promote crosslinking. (D) The final construct as a rectangular grid-shaped structure.

FIG. 8C Bioprinting process—The bioprinted constructs being irradiated with visible light after extrusion to promote crosslinking.

FIG. 8D Bioprinting process—The final construct as a rectangular grid-shaped structure FIG. 9 Bar graph displaying calculated cell viability. Immediately after bioprinting, constructs exhibit a cell viability close to 100%, while after 72 h of incubation, cell viability is close to 70%.

DETAILED DESCRIPTION OF THE INVENTION

Figure 1A:
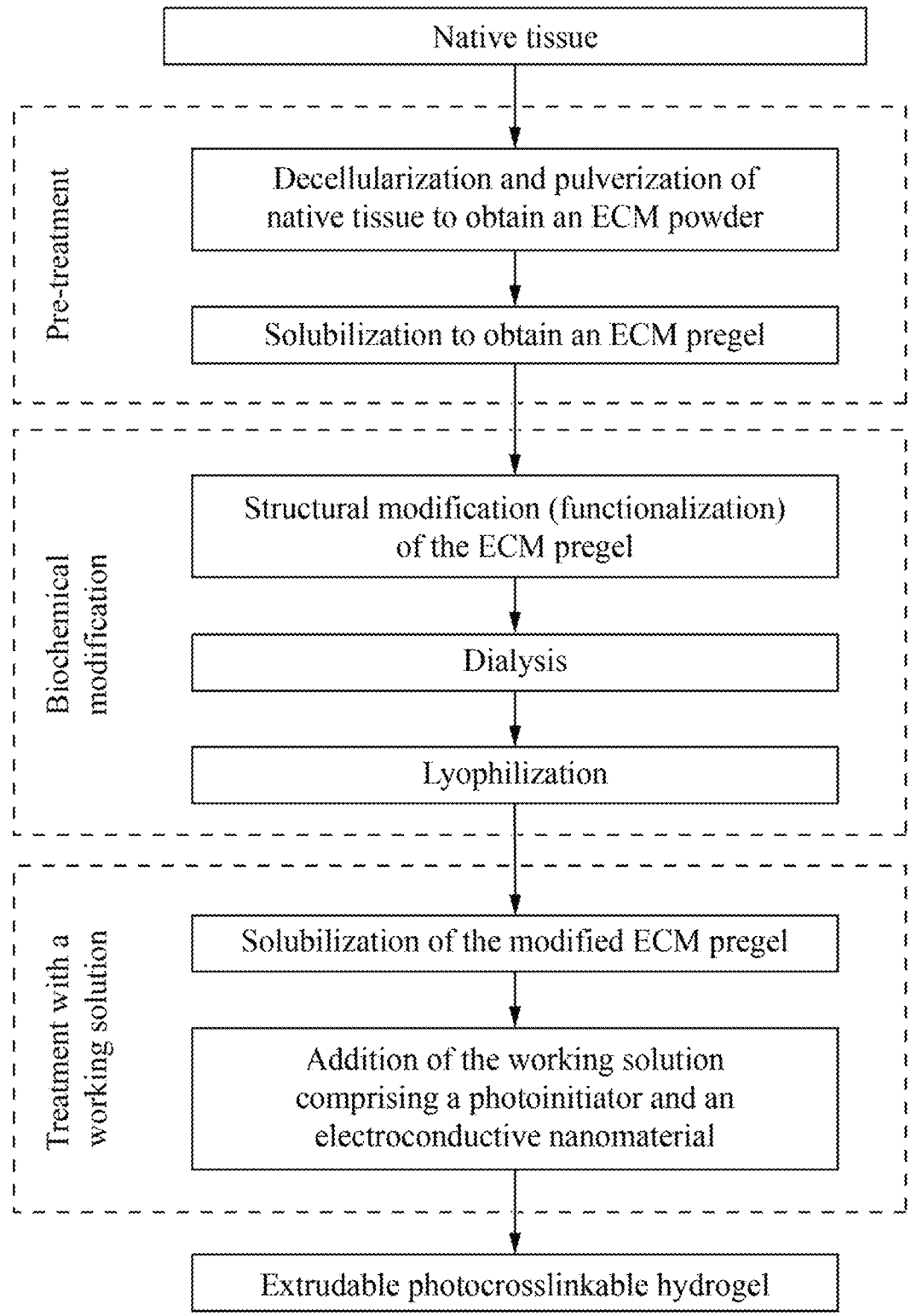
FIG. 1A Method for preparing an extrudable photocrosslinkable hydrogel—General flowchart.

The present invention relates to an extrudable photocrosslinkable hydrogel comprising a biochemically-modified extracellular matrix (ECM) with an electroconductive nanomaterial embedded; a photoinitiator and a solvent; a method for the preparation of the extrudable photocrosslinkable hydrogel starting from decellularized extracellular matrices (dECMs); and its applications thereof.

Unless defined otherwise, all technical and scientific terms used herein have the same meaning as commonly understood by one of ordinary skill in the art to which this disclosure belongs. It is also to be understood that the terminology used herein is for the purpose of describing particular embodiments only, and is not intended to be limiting. Before the present disclosure is described in greater detail, it is to be understood that this disclosure is not limited to particular embodiments described, and as such may, of course, vary.

As used in the Specification and claims, the singular form "a," "an," and "the" include plural references unless the context clearly dictates otherwise.

Extrudable Photocrosslinkable Hydrogel

In a first aspect, an extrudable photocrosslinkable hydrogel is described. An extrudable photocrosslinkable hydrogel according to the present disclosure comprises a biochemically-modified extracellular matrix (ECM), an electroconductive nanomaterial, a photoinitiator and a solvent. In a particular aspect of the hydrogel, an electroconductive nanomaterial is embedded in the biochemically-modified ECM.

An extrudable photocrosslinkable hydrogel according to the present disclosure comprises:
- a biochemically modified ECM at a concentration ranging from 5 to 50 mg/mL;
- an electroconductive nanomaterial at a concentration ranging from 0.10 to 1 mg/mL;
- a photoinitiator at a concentration ranging from 0.1 to 5 mg/mL; and
- a solvent.

The hydrogel according to the present invention has photocrosslinking, thermal sensitivity and electroconductive properties which allow it to mimic the native environment of cells within tissues. Some advantages of the hydrogel are its versatility (i.e., it mimics different kinds of tissues), its biocompatibility, mechanical properties, printability and electroconductivity. A superior biocompatibility is provided by the presence of several biomolecules capable of conferring a therapeutic potential to the hydrogel, for example, they may provide antimicrobial, immunomodulatory, anti-aging, antioxidant, or anti-inflammatory effects, among others, which are key to assure that the regeneration process is accelerated. In terms of the mechanical properties, the hydrogel offers the possibility to adjust the Young's modulus according to that of the tissue to regenerate. Matching the mechanical properties of the tissue is of the utmost importance to assure proper cell proliferation and tissue remodeling. Printability facilitates forming constructs with sufficient shape fidelity after printing to ultimately maintain the integrity of the material during maturation and even post-implantation. Finally, electroconductivity is useful to circulate currents locally and to accelerate the rates of cell proliferation, cell differentiation, signal propagation and angiogenesis.

In particular, the ECM is composed of proteins (such as laminin, elastin and collagen), glycosaminoglycans (like hyaluronic acid and dermatan sulphate) and growth factors (like vascular endothelial growth factor VEGF and fibroblast growth factor FGF). The ECM provides cell anchorage sites for cells and can direct cell behavior. The ECM can be isolated from liver, urinary bladder, intestine, heart, lung, kidney placenta, skin, omentum, cartilage, and any other solid tissue. Combinations of ECMs isolated from different tissues can be also used. Preferred ECM is isolated from small intestine submucosa (SIS) and placental amniotic membrane (PAM). Given their heterogeneous composition, ECMs provide cells with a very similar environment to that found in vivo. Hydrogels composed of only one or two natural materials fail to provide such native environment in vitro.

The ECM can be structurally modified to enhance or provide certain capabilities when transformed into hydrogels. One of such capabilities is crosslinking, in which covalent bonds can be created between and among the polymer chains of a hydrogel. These covalent bonds can increase the mechanical stiffness of the hydrogels, thus providing them with enhanced structural stability. Furthermore, these biochemical modifications often allow precise control of hydrogel's crosslinking degree, otherwise, this is very difficult or not possible to achieve. Furthermore, biochemical modification often enhances the thermosensitivity properties of ECMs, which results in more structurally stable hydrogels at physiological temperature.

In the present invention, the ECM is biochemically modified by adding chemical groups such as methacrylate, acrylate, divinyl sulfone, thiol, and mixtures thereof. Preferred chemical groups are acrylate and variants thereof e.g., ethyl acrylate (C5H8O2), ethyl methacrylate (C6H10O2), and methyl methacrylate (C5H8O2). Biochemical modification achieved with chemical groups provides the possibility to crosslink the modified hydrogel upon exposure to ultraviolet (UV) or visible light in the presence of a photoinitiator molecule (this process is named photocrosslinking). Thus, this modification allows to precisely tune the mechanical properties of the hydrogel by modulating the photoinitiator's concentration and the energy dosage received from a UV or visible light source. Photocrosslinking is mainly due to the double carbon-carbon bonds present in the added functional groups, which are unstabilized in the presence of free radicals. The unstable functional groups tend to form covalent bonds with other functional groups of a different or the same polymer monomer. In a particular embodiment of the present invention, the ECM is modified with methacrylic acid or methacrylic anhydride, which results in methacryloyl-modified ECM proteins.

The biochemically modified ECM may be at a concentration from 5 to 50 mg/mL; from 10 to 40 mg/mL, from 15 to 30 mg/mL, from 25 to 35 mg/mL, or from 30 to 50 mg/mL in the hydrogel's composition. In a particular embodiment, the biochemically-modified ECM is at a concentration of 30 mg/mL in the hydrogel's composition.

In another particular embodiment, the biochemically-modified ECM is lyophilized by methods and conditions necessary for lyophilization to be ensured. For example, wherein the modified ECM is stored at −80° C. for at least 12 h and subsequently lyophilized at a pressure between 0.05 and 0.20 mbar for 24 to 96 h.

The electroconductive nanomaterial is a 2D nanoscale material with the capability of conducting electricity in an unimpeded manner. The electroconductive nanomaterial provides the hydrogel with electric conductivity, which in turn, provides control of the mechanical stiffness of the hydrogel. In addition, electric conductivity allows the controlled release of therapeutic molecules and dosage optimization (quantity and timing), and ultimately induces tissue regeneration. Other advantages given by the electroconductive nanomaterials are that they allow obtaining hydrogels which promote the maturation and regeneration of tissues requiring specific electrical cues such as cardiac, muscular and neural tissue. In one embodiment, the electroconductive nanomaterial is embedded into the biochemically modified ECM.

The electroconductive nanomaterial is selected from any conductive nanomaterial that has nanometric length in two dimensions, including, without being limited to graphene, borophene, graphyne, silicene, germanene, stanine and variants or mixtures thereof. Preferred nanomaterials are graphene and variants thereof e.g., graphene nanoribbons, graphene oxide, reduced graphene oxide and graphene nanoparticles. Particularly, a preferred electroconductive nanomaterial is graphene oxide.

The electroconductive nanomaterial may be at a concentration ranging from 0.10 to 1 mg/mL, from 0.10 to 0.25 mg/mL, from 0.2 to 0.3 mg/mL, from 0.25 to 0.5 mg/mL or from 0.5 to 1 mg/mL in the hydrogel's composition. In a particular embodiment, the electroconductive nanomaterial is at a concentration of 0.25 mg/mL in the hydrogel's composition.

Finally, a photoinitiator is essential for photocrosslinking reactions as it can dissociate into free radicals, which facilitates the formation of covalent bonds between the biochemically modified ECM proteins. Photoinitiators produce free radicals as by-products of their degradation when irradiated with UV or visible light. Free radicals catalyze the formation of covalent bonds between the chemical groups of the modified ECM (for example, acrylate or any of its variants), which results in enhanced mechanical stiffness. The main advantage of photoinitiators that produce free radicals upon exposure to visible light is their biocompatibility, since other light sources such as UV have demonstrated to be harmful for cells.

According to the present disclosure, photoinitiator molecules are those which can degrade upon exposure to light in the visible range of the electromagnetic spectrum, including, but not limited to dyes, pigments, chromophores, and fluorophores. Photoinitiators are selected from, without being limited to riboflavin, ruthenium, 1-[4-(2-hydroxyethoxy)-phenyl]-2-hydroxy-2-methyl-1-propane-1-one (IRGACURE), lithium phenyl-2,4,6-trimethylbenzoylphosphinate (LAP) and mixtures thereof. A preferred photoinitiator is riboflavin.

The photoinitiator may be at a concentration of 0.1 to 5 mg/mL, from 0.1 to 0.5 mg/mL, from 0.5 to 1.0 mg/mL, from 0.1 to 1.0 mg/mL, or from 1.0 to 5 mg/mL in the hydrogel's composition. In a particular embodiment, the photoinitiator is at a concentration of 0.5 mg/mL in the hydrogel's composition.

The hydrogel optionally comprises bioactive molecules immobilized on the surface of the electroconductive nanomaterials. Bioactive molecules are those capable of conferring a therapeutic potential to the hydrogel, for example, they may provide antimicrobial, immunomodulatory, anti-aging, antioxidant, or anti-inflammatory effects, among others. When immobilized on the surface of electroconductive materials, these bioactive molecules can be released on command as explained above. Bioactive molecules are selected from but not limited to antibiotics, antimicrobial peptides, flavonoids, flavones, isoflavones, flavonols, polyphenols, anthracyclines, vinca alkaloids, epipodophyllotoxins lignans, camptothecin derivatives, toxoids and mixtures thereof.

Preferred bioactive molecules are short peptides (i.e., having <50 amino acids), selected from, without being limited to cecropin A, cinnamycin, β-defensin, duramycin, melittin, nisin, pediocin, among others. These peptides are natural alternatives to synthetic drugs, with similar efficacy but fewer adverse effects. In turn, peptides are considered safer therapeutics than drugs. Moreover, these peptides can be precisely distributed inside the hydrogel and released on command, allowing significant control over dosages at specific targets over time.

Bioactive molecules may be immobilized at concentrations ranging from ng/ml to u g/mL. This range is provided taking into account the possible differences between the biological activity of each biomolecule to be evaluated and their possible harmful limit concentration for cells.

The hydrogel may further comprise natural polymers, which are preferred over synthetic ones for hydrogel formulation because of their high biocompatibility. However, one important challenge when incorporating natural polymers into hydrogels is their lack of mechanical and structural stability, which translates into, both, poor printability and deficient shape fidelity of the resulting constructs. Natural polymers that can be combined with the hydrogel according to the present invention are selected from, without being limited to, chitosan, gelatin, collagen, hyaluronic acid, laminin, fibronectin, alginate and mixtures thereof. In a preferred embodiment the natural polymer is chitosan.

Furthermore, in the embodiments wherein the hydrogel comprises natural polymers, they are at a final concentration ranging from 5 to 50 mg/mL of the hydrogels composition, from 5 to 20 mg/mL, from 10 to 25 mg/mL, or from 20 to 50 mg/mL. In a particular embodiment, the natural polymer is at a concentration of 20 mg/mL.

The solvent according to the present disclosure corresponds to an acid mixed with a working solution consisting of cell culture medium at a pH ranging between 7 and 9 and water. Particularly the solvent comprises an acid at a concentration ranging from 0.005 to 0.02 M, mixed with the working solution at proportions between 1:0.5 and 1:10, respectively.

Suitable acids for the solvent are strong acids. Particularly the suitable acids are selected from, without being limited to acetic acid or hydrochloric acid. In a particular embodiment, the solvent comprises acetic acid at a concentration of 0.5 M.

Suitable cell culture media for the hydrogel are selected from, without being limited to Dulbecco's Modified Eagle's Medium (DMEM), MEM, F12 or any other necessary to culture an specific type of cell. In a preferred embodiment, the cell culture medium in the solvent is Dulbecco's Modified Eagle's Medium (DMEM).

In a preferred embodiment, the extrudable photocrosslinkable hydrogel according to the present disclosure is:
  lyophilized biochemically-modified ECM at a concentration from 25 to 35 mg/ml;
  an electroconductive nanomaterial at a concentration from 0.2 to 0.3 mg/mL;
  a photoinitiator molecule at a concentration from 0.1 to 1.0 mg/ml;
  a natural polymer at a concentration from 10 to 25 mg/mL; and
  a solvent comprising acetic acid at a concentration of 0.005 to 0.02 M mixed with a working solution of a cell culture medium at a pH between 7 and 9 at a proportion between 1:0.5 and 1:10, respectively.

In another preferred embodiment, the extrudable photocrosslinkable hydrogel according to the present disclosure is:
  lyophilized biochemically-modified ECM at a concentration of 30 mg/mL;
  an electroconductive nanomaterial at a concentration of 0.25 mg/mL;
  a photoinitiator molecule at a concentration of 0.5 mg/mL;
  a natural polymer at a concentration of 20 mg/mL; and
  a solvent comprising acetic acid 0.5 M mixed with a working solution of a cell culture medium at a pH 8.5 at a proportion between 1:0.5 and 1:10, respectively.

In a particular embodiment, the hydrogel as disclosed herein comprises human foreskin fibroblasts (HFF) at a final concentration of 750,000 cells/mL.

Properties of the Hydrogel

Before crosslinking by light or temperature, the hydrogel has a dynamic viscosity ranging from 0.1 to 10,000 Pa*s, mainly dependent on the ECM concentration (between 5 and 50 mg/mL) and the shear rate. Upon crosslinking, either by light, temperature or a combination of both, the storage modulus of the hydrogels is between 100 and 2,000 Pa, which depends on the energy dosage given when exposing the material to visible light and on the incubation time when raising the temperature to 37° C.

Specific values of these parameters must be chosen depending on the final application. For bioprinting and in situ defect filling applications, the mechanical properties of the tissue to be printed must be considered for tuning the viscosity and stiffness of the hydrogel, as well as for designing a crosslinking scheme (i.e., energy dosage given by exposure to visible light and incubation time at 37°) C.

The hydrogels according to the present invention, the bioink (hydrogel embedded with cells for use in bioprinting), and the extruded crosslinked constructs obtained from them, may be used in a variety of applications, alone or in combination with conductive controlled release of therapeutic molecules. Some of the applications are, without being limited to regenerative applications, adhesives for different tissues, research applications and 3D structures. For example regenerative applications include electroconductive extrudable hydrogels for in situ defect-filling, electroconductive scaffolds, conductive grafts, in situ printed tissue or organs, as well as structures for growing and maintaining cells; adhesives include bone bioadhesives; and research applications include organ and tissue models, therapeutic models, disease models, infection models, and regenerative models.

Method for Preparing an Extrudable Photocrosslinkable Hydrogel

According to the present invention a method for preparing an extrudable photocrosslinkable hydrogel comprises biochemically modifying an ECM pregel; and treating it with a working solution comprising a photoinitiator and an electroconductive nanomaterial. A general scheme of the method is shown in FIG. 1A.

Pre-Treatment

An ECM pregel can be prepared by different methods. Generally, these methods vary depending on the tissue of origin from which the ECM is to be isolated. In particular, native tissue should necessarily be treated to remove all cellular material from the host organism. The resulting set of proteins, which include various types of collagen, laminin and elastin, and biological molecules, such as glycosaminoglycans and growth factors, compose the ECM. In general, the treatment or pretreatment of the native tissue includes the steps of decellularization and pulverization, wherein decellularization removes all cellular material from the organism of origin, including genetic and structural components of cells, yielding only the matrix that builds up the tissue of interest. Decellularization depends largely on the type of tissue. According to the present disclosure, decellularized ECM can be obtained by any method known in the art, for example Saldin et al (Saldin et al. 2017. Extracellular matrix hydrogels from decellularized tissues: Structure and function. Acta Biomaterialia; 49:1-15), describes the formation and physical and biological characterization of extracellular matrix hydrogels. After decellularization is completed, tissue samples are freeze-dried and pulverized, and the resulting product is a fine powder of the ECM used to provide structural support, as well as chemical and mechanical cues to cells embedded in the native state of the tissue.

Once the ECM powder is obtained, it undergoes a solubilization process which yields an ECM pregel. Solubilization can be done in a solubilization solution consisting of an acid and a proteolytic enzyme. The ECM powder is solubilized at concentrations ranging from 1 to 30 mg/mL in the acidic solution. The acid is selected from, without being limited to, hydrochloric acid (HCl) and acetic acid ($CH_3COOH$) and mixtures thereof. The acid is at concentrations varying from 0.01 to 0.5 M. The proteolytic enzyme cleaves the ECM proteins into smaller fragments, which facilitates obtaining a homogeneous solution. The proteolytic enzyme is selected from pepsin, zymogens, collagenase, urokinase, activated protein C, chymotrypsin, gamma-glutamyltransferase 1, lactoferrin, dipeptidase E, carboxypeptidase Y, papain and mixtures thereof. The proteolytic enzyme is added to the solubilization solution at concentrations varying from 0.5 to 5 mg/mL. In a particular embodiment the proteolytic enzyme is pepsin. Solubilization is carried out at temperatures between 4 and 37° C. for 6 to 72 h. However, as explained above, concentrations and conditions for ECM solubilization largely depend on the protein content of the tissue of origin, so no universal method is available for solubilizing every kind of tissue powder. In a particular embodiment the solubilization process is carried out at room temperature (~22°) C. for 72 h.

Biochemically Modifying an Extracellular Matrix (ECM) Pregel

The polymer chains composing the solubilized ECM pregel can be structurally modified to enhance or provide certain capabilities when the hydrogels are formed, named for the purposes of this application as a biochemical modification of the ECM. For example, biochemical modification to enhance the crosslinking capabilities of hydrogels can be done with, but are not limited to, chemical groups such as methacrylate, acrylate, divinyl sulfone and thiol. Modifications with these chemical groups confer a crosslinking capability in the resulting hydrogel upon exposure to ultraviolet (UV) or visible light in the presence of a photoinitiator molecule (namely photocrosslinking). In a particular embodiment, an ECM pregel is biochemically modified with methacrylic acid to obtain methacryloyl-modified ECM.

The biochemically-modified ECM pregel could be dialyzed to remove unreacted reagents and undesired byproducts of the reactions. The dialysis process could last for 48 to 120 h, in a solution which is between 100 and 500 times the volume of the modified pregel being dialyzed. This solution generally consists of the acid at the same concentration in which the solubilization and biochemical modification steps took place (e.g., acetic acid at a 0.5 M concentration or HCl at a 0.1 M concentration). The acidic solution in which the dialysis takes place must be replaced between every 3 h to 12 h. In a particular embodiment, the biochemically-modified ECM pregel is dialyzed for 48 h against 0.5 M acetic acid. In this timespan, the acidic solution is replaced every 12 h and its volume is always 100 times the volume of modified ECM pregel being dialyzed.

Immediately after dialysis, the biochemically modified ECM pregel is generally lyophilized in order to obtain the pregel in a form of a dry porous matrix. This step is useful to prepare the hydrogel at a specific concentration, not depending on the initial concentration at which the solubilization step was performed. Prior to lyophilization, biochemically modified ECM pregels must be kept at −80° ° C. for at least 12 h. Subsequently, the pregels can be lyophilized at a pressure between 0.05 and 0.2 mbar for between 24 and 72 h.

Treatment of the Modified ECM Pregel with a Working Solution

The most abundant protein in ECM-based hydrogels is collagen, which features temperature-driven self-assembly at physiologic conditions of temperature (37°) C. and pH (~7). This self-assembly of collagen fibers is a non-covalent method of crosslinking, which means it can stiffen hydrogels but in a weak and reversible manner. Thus, the lyophilized biochemically modified ECM matrix is solubilized in an acidic solution and its pH must be subsequently raised to neutral in order to prepare a hydrogel. Solubilization can be done in acetic acid or hydrochloric acid, at concentrations varying from 0.01 to 0.5 M, and pH must be raised to 7 by addition of a base, such as sodium hydroxide or sodium bicarbonate, at concentrations ranging from 0.1 to 10 M or addition of a strong buffer, which should be able to yield a final pH close to 7 while not resulting in a harmful environment for the cells that will later be embedded in the hydrogel. Suitable buffers according to the present disclosure include, without being limited to trisaminomethane and trisaminomethane hydrochloride at concentrations ranging from 10 to 500 mM. In a particular embodiment, the strong buffer is trisaminomethane hydrochloride at a final concentration in the hydrogel of 50 mM. Strong buffer may be contained in a working solution with a photoinitiator molecule, electroconductive nanomaterials, and therapeutic molecules.

The solubilized biochemically-modified ECM pregel is then treated with a working solution incorporated at a ratio between 1:0.5 and 1:10, respectively. During the incorporation, both solutions and the subsequently obtained mixture (hydrogel) must be kept between 2 and 8° C. and protected from light in order to avoid unwanted crosslinking reactions. According to the present disclosure, the working solution for obtaining an extrudable photocrosslinkable hydrogel comprises a cell culture medium, a photoinitiator, an electroconductive nanomaterial, optionally a strong buffer for pH regulation and, optionally a therapeutic molecule.

The photoinitiator and the electroconductive nanomaterials shall be first dispersed into the working solution. For obtaining the working solution according to the present disclosure, the photoinitiator and the electroconductive nanomaterial are incorporated into the working solution at a concentration of between 0.1 and 5 mg/mL, and between 0.1 and 1 mg/mL, respectively. Full dispersion must be guaranteed before incorporating the working solution with the solubilized biochemically-modified ECM. In a particular embodiment, the solubilized biochemically-modified ECM pregel is mixed at a 1:1 ratio with a working solution consisting of DMEM cell culture media containing riboflavin as photoinitiator at a 0.5 mg/mL concentration, graphene oxide at a 0.25 mg/mL concentration and trisaminomethane hydrochloride at a 100 mM concentration.

According to the present disclosure, bioactive molecules are optionally added to the hydrogel. Bioactive molecules must be first immobilized on the surface of the electroconductive nanomaterial, which can be done with amine-amine or carboxyl-amine crosslinkers, depending on the chemical structure of the bioactive molecule. These crosslinkers can include but are not limited to PEG, ethyl-3-[3-dimethylaminopropyl]carbodiimide hydrochloride (EDC), N-hydroxysuccinimide (NHS) and glutaraldehyde. Immobilization reactions are carried out at molar ratios between the bioactive molecules and the electroconductive nanomaterials ranging from 1:1 to 20:1, respectively. In a particular embodiment, immobilization reactions of the bioactive molecules on the surface of electroconductive nanomaterials are performed at a 10:1 ratio, respectively, and utilizing EDC and NHS as crosslinkers.

Optional natural polymers are incorporated into the hydrogel at the moment of solubilizing the biochemically-modified ECM or when mixing the biochemically-modified ECM pregel with the working solution, at a concentration of 20 mg/mL.

In addition, when adding the working solution to the biochemically-modified ECM pregel, the pH becomes close to neutral, which allows embedding cells and obtaining a bioink (hydrogel embedded with cells) for use in bioprinting.

Bioprinting and Constructs

The hydrogel provides an environment that mimics the native environment of cells inside tissues, thus, when mixed with a cell suspension, the resulting bioink allows bioprinting a diversity of customized and multifunctional constructs with cell viability, suitable for regeneration of different tissues and organs. For example bioinks capable of conducting electricity can promote the maturation and regeneration of tissues which require specific electrical cues such as cardiac, muscular and neural. Bioprinted constructs may serve as scaffolds, grafts, organ models and structures for growing and maintaining cells, amongst others.

EXAMPLES

Throughout the description, where hydrogels are described as having, including, or comprising specific components, it is contemplated that these compositions may also consist essentially of, or consist of, the recited components. Further, it should be understood that the order of steps or order for performing certain actions are immaterial so long as the invention remains operable, unless explicitly explained. Moreover, two or more steps or actions may be conducted simultaneously. In light of the foregoing description, the specific non-limiting examples presented below are for illustrative purposes and not intended to limit the scope of the invention in any way.

Example 1. Method for Producing a Hydrogel from SIS or PAM

Figure 1B:
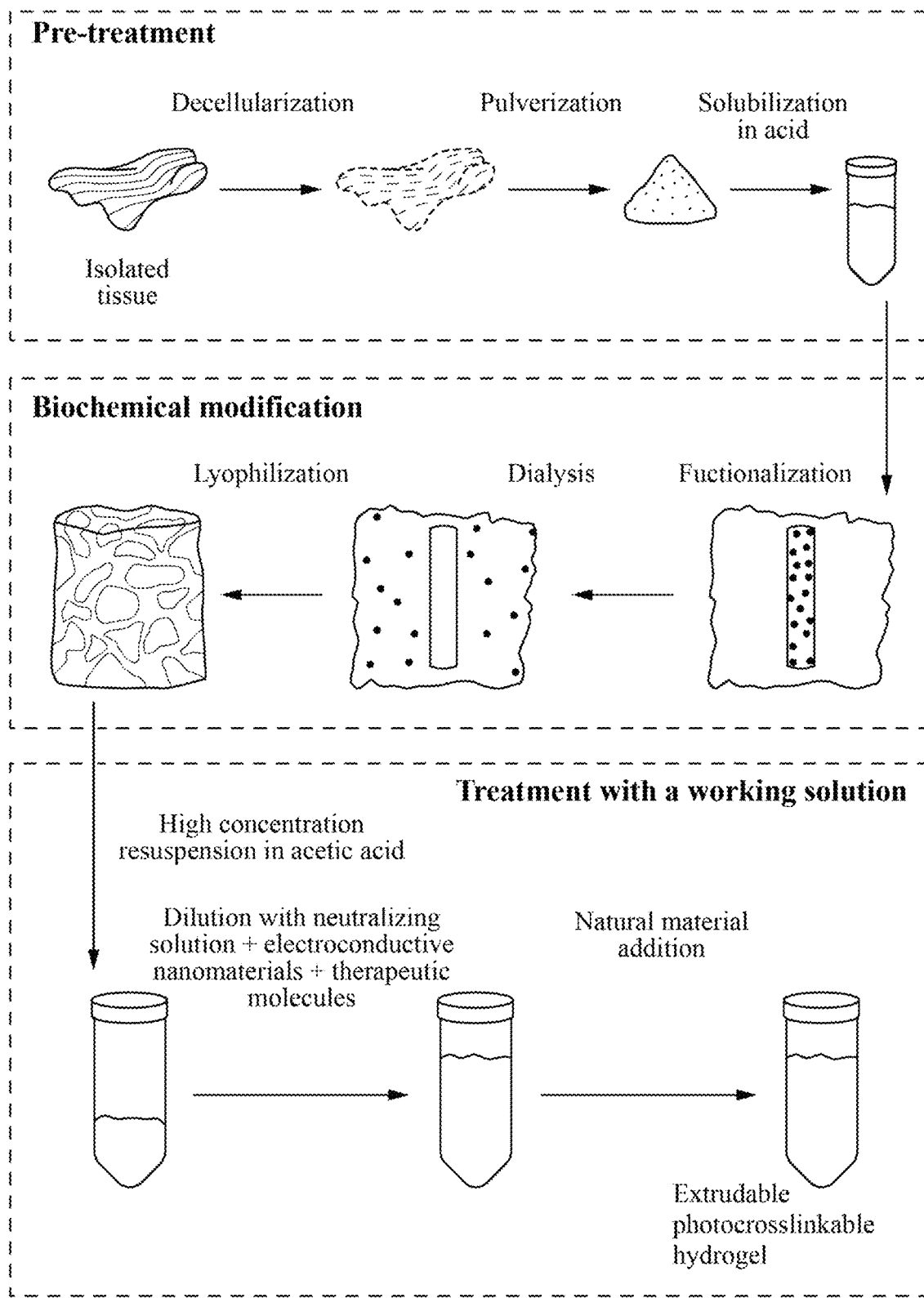
FIG. 1B Method for preparing an extrudable photocrosslinkable hydrogel—(B) Schematic method of embodiments in Examples 1, 5 and 6.

An embodiment of the method for producing a hydrogel according to the present disclosure is illustrated in FIG. 1B.

In particular, ECM powder from small intestinal submucosa (SIS) or porcine amniotic membrane (PAM) was solubilized at a 1% (w/v) concentration at room temperature (~22° C.) under constant magnetic stirring. ECM powder from PAM was solubilized for 48 h, while the ECM powder from SIS was solubilized for 24 h. For both ECMs, solubilization solution consisted of 0.5 M acetic acid with porcine pepsin at a concentration of 1 mg/mL. After this procedure, a solubilized ECM-pregel was obtained.

Biochemical modification of the solubilized ECM pregel was performed by using methacrylic acid, which resulted in methacryloyl-modified ECM proteins. The process consisted of functionalizing the solubilized ECM pregel with methacrylic acid in the presence of EDC and NHS. The resulting product is dialyzed and lyophilized.

For functionalization, EDC, NHS, and the methacrylic acid were solubilized in a 50% (v/v) N,N-dimethylformamide (DMF) solution and the mixture was heated at 40° C. for 15 min under constant magnetic stirring. This was done to activate and stabilize the carboxyl groups of methacrylic acid with the aid of EDC and NHS. After activation was completed, the mixture of methacrylic acid, EDC and NHS was added to the solubilized ECM pregel and left to react for 24 h under constant magnetic stirring at 4° C. This step resulted in methacryloyl-modified ECM pregels. Next, dialysis was performed to the methacryloyl-modified ECM pregels by loading them into dialysis cassettes and submerging these in acetic acid at a 0.5 M concentration. The volume of the acetic acid solution was 100 times the volume of the pregel. This process was held for 48 h, time in which the acetic acid solution was replaced with a fresh solution every 12 h.

After the dialysis process is completed, the methacryloyl-modified ECM pregels were frozen at −80° C. for at least 12 h and subsequently lyophilized to remove its liquid content and moisture. The product obtained was a white cloud-like 3D matrix. For obtaining a hydrogel, a 0.02 M acetic acid solution was used for the solubilization of the resulting lyophilized methacryloyl-modified ECM. The white cloud-like 3D matrices were solubilized at twice the desired final concentration of the hydrogel. For example, for preparing a hydrogel with modified ECM at a 20 mg/mL final concentration, solubilization must occur at a 40 mg/mL concentration of modified ECM in the acetic acid solution.

A working solution was prepared and incorporated into the solubilized ECM at a 1:1 proportion, while maintaining the temperature of the mixture below 10° C. and protecting it from light. This working solution consisted of DMEM cell culture medium supplemented with 10% (v/v) fetal bovine serum and 100 mM trisaminomethane hydrochloride at a pH of 8.5, and subsequently incorporated graphene oxide and riboflavin, as electroconductive nanomaterial and photoinitiator, at a concentration of 0.5 mg/mL and 1 mg/mL, respectively.

Example 2. Compositions of the Hydrogel

The following hydrogels can be obtained by following the method of Example 1:

| Component | | A1 | A2 | A3 | A4 | A5 |
|---|---|---|---|---|---|---|
| Lyophilized biochemically-modified ECM | | 30 mg/mL | 30 mg/mL | 25 mg/mL | 25 mg/mL | 20 mg/mL |
| Electroconductive nanomaterial | | 0.25 mg/mL | 0.25 mg/mL | 0.25 mg/mL | 0.5 mg/mL | 0.5 mg/mL |
| Photoinitiator molecule | | 0.5 mg/mL | 0.25 mg/mL | 0.5 mg/mL | 0.5 mg/mL | 0.5 mg/mL |
| Solvent | Acetic acid | 0.01M | 0.01M | 0.01M | 0.01M | 0.01M |
| | Cell culture medium | 50% v/v | 50% v/v | 50% v/v | 50% v/v | 50% v/v |

Example 3. Physicochemical Characterization of the Hydrogel

Rheological Properties

The rheological behavior of the methacryloyl-modified ECM hydrogel of Example 1 was determined by flow and time sweep experiments to assess changes in the storage (G') and loss (G") moduli, before and after exposure to blue light. Experiments were performed with a parallel plate geometry (20 mm) and at 22° C. (Discovery Series Hybrid Rheometer-1, TA Instruments, New Castle, DE, USA). Flow sweep was performed between 0.01 and 200 Hz without exposure to blue light. Time sweep was performed at 1 Hz and 1% strain by maintaining a 1 mm gap. For each formulation, G' and G" were measured for 180 s. The same experiment was repeated for the samples in the presence of irradiation.

Figure 2A:
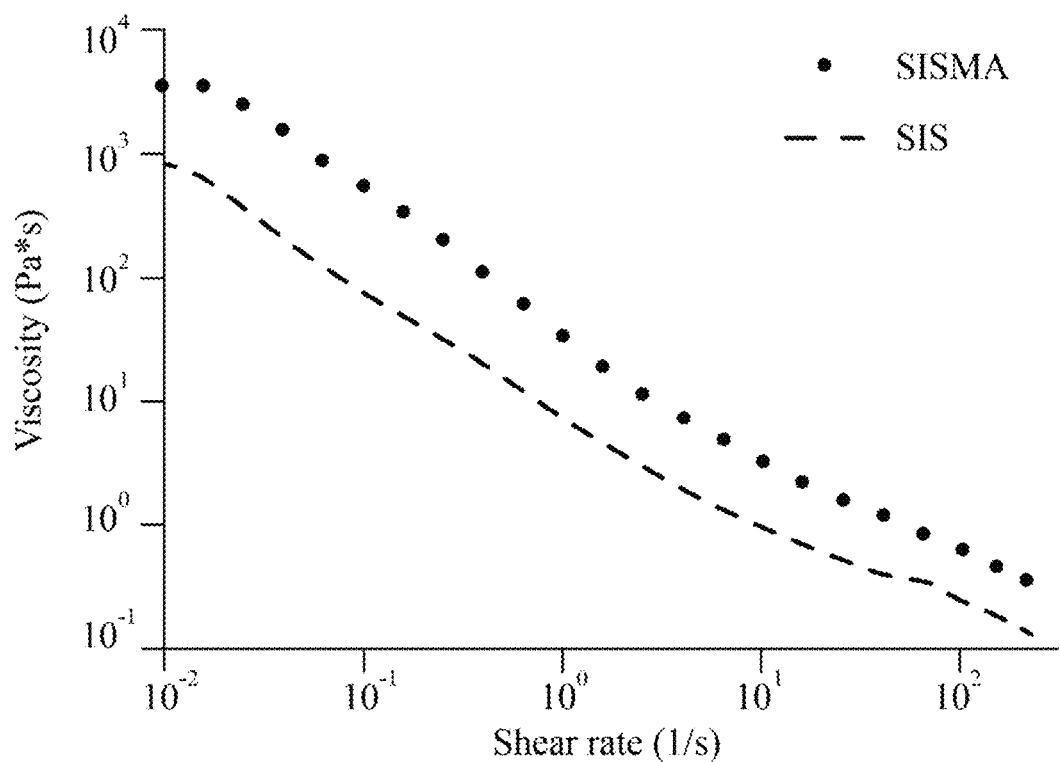
FIG. 2A Viscosity vs. shear rate plot in logarithmic scale—ECM (SIS) and methacryloyl-modified ECM (SISMA).
Figure 2B:
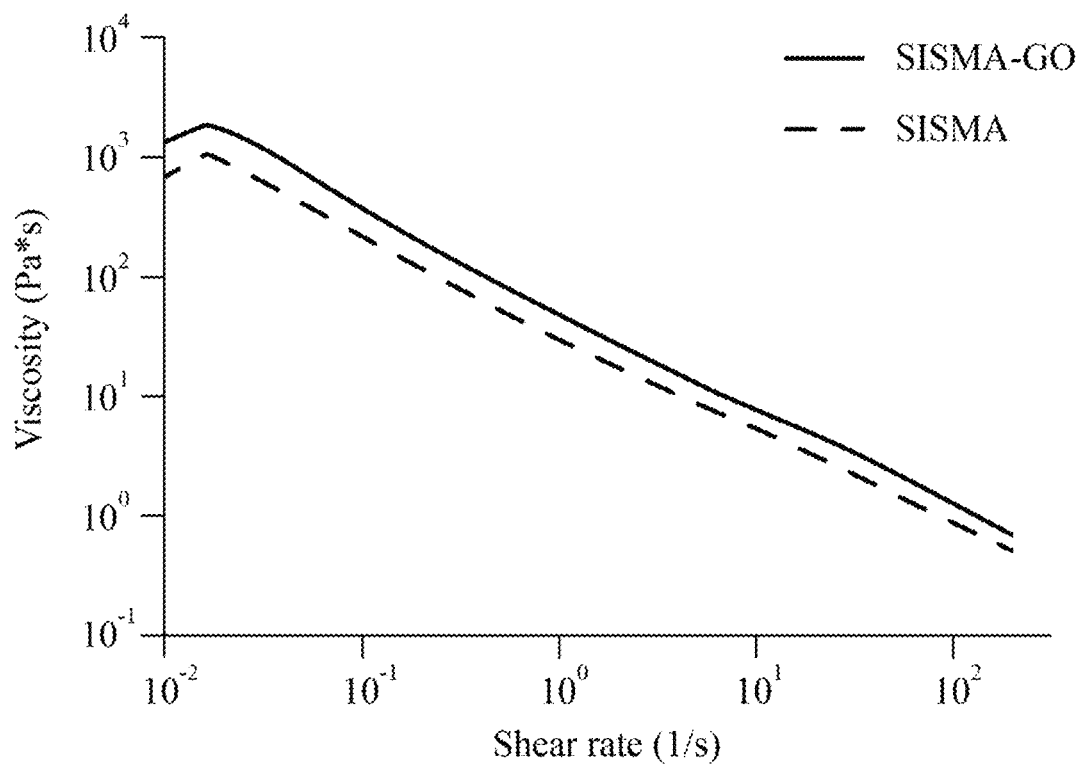
FIG. 2B Viscosity vs. shear rate plot in logarithmic scale—Methacryloyl-modified ECM hydrogels (SISMA) and methacryloyl-modified ECM hydrogels with graphene oxide (SISMA-GO).

FIG. 2A and FIG. 2B show the viscosity vs. shear rate plot in logarithmic scale for solely ECM (named SIS in FIG. 2A) and the methacryloyl-modified ECM hydrogel of Example 1 (named SISMA in FIG. 2A). The flow sweep experiment showed shear-thinning behavior for all formulations, as viscosity decreased as a function of increasing shear rate. This is a highly desirable characteristic for hydrogels to be used in applications that require extrusion through a needle or a nozzle, such as 3D bioprinting, injectable hydrogels and in situ defect filling.

Both SIS and SISMA hydrogels exhibited shear thinning behavior, as viscosity decreased when shear rate increased. Similarly, methacryloyl-modified ECM hydrogels with and without graphene oxide (GO) exhibited shear thinning behavior as well (FIG. 2B).

Figure 3A:
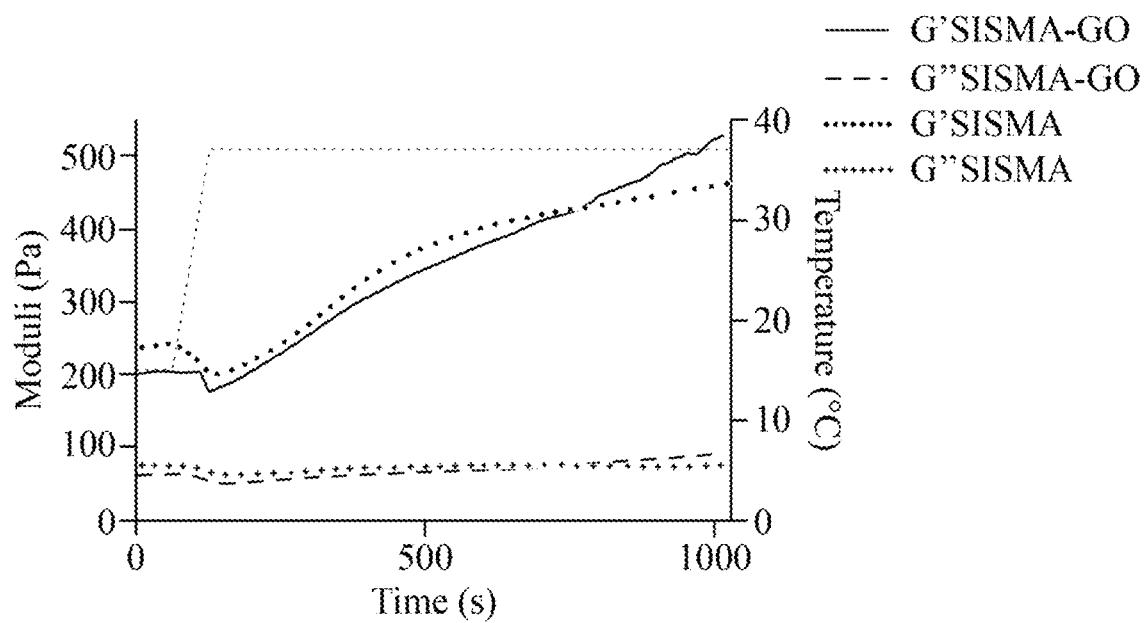
FIG. 3A Measurement of storage (G') and loss (G") moduli to identify changes in the behavior of the hydrogels SISMA and SISMA-GO—Temperature sweep rheological test performed to study the behavior of the hydrogels under changes of temperature.

FIG. 3A shows the results of a temperature sweep rheological test performed to study the behavior of the hydrogels under changes of temperature. For this test, the temperature of the sample was quickly raised from 15° C. to 37° C. and maintained at this temperature for approximately 15 min. Changes in the storage (G') and loss (G") moduli were measured to identify changes in the behavior of the hydrogels. Results showed a highly temperature-dependent behavior, as the storage modulus (G') of methacryloyl-modified ECM hydrogels with and without graphene oxide (GO) increased up to 2.5 times after temperature was raised to mimic physiological conditions. Storage modulus (G') is also termed as elastic modulus, as it can be directly related to the stiffness of a hydrogel. For this test, hydrogels were not exposed to light in the visible range, solely to changes in temperature.

Figure 3B:
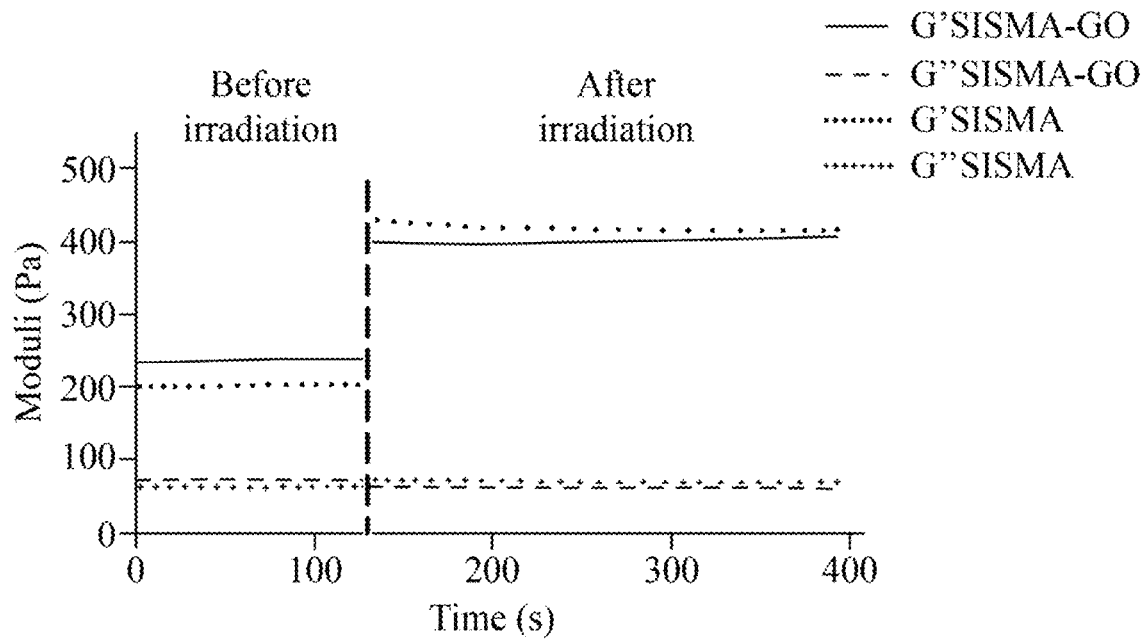
FIG. 3B Measurement of storage (G') and loss (G") moduli to identify changes in the behavior of the hydrogels SISMA and SISMA-GO—Time sweep rheological test performed at 15° C. before and after exposure to light in the visible range (irradiation) to promote crosslinking.

FIG. 3B illustrates the results of a time sweep rheological test performed at 15° C. before and after exposure to light in the visible range to promote crosslinking. Both hydrogels increased their storage modulus (G') after irradiation, which suggests crosslinking reactions as a result of exposure to light.

Manual Extrusion Tests

Figure 4:
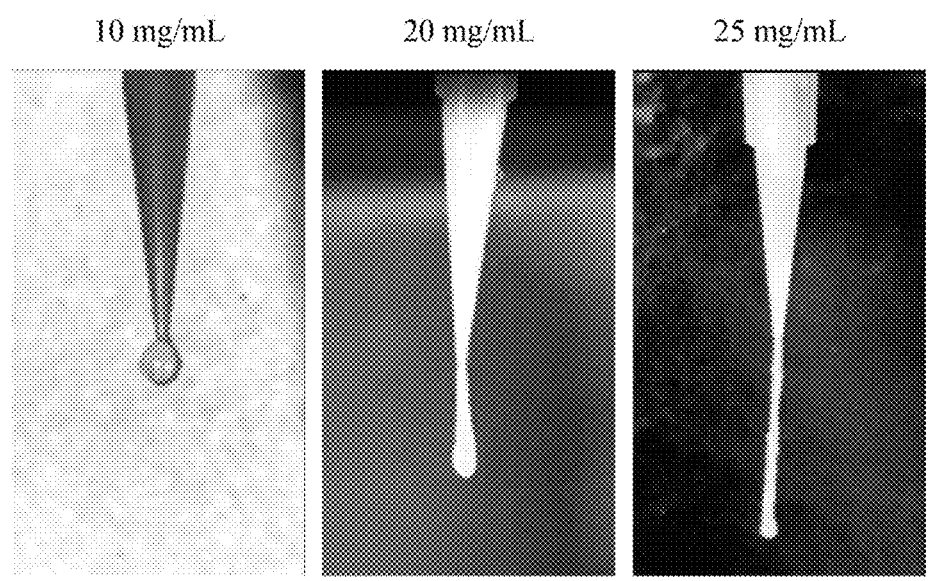
FIG. 4 Manual extrusion tests. Three different formulations of the methacryloyl-modified ECM hydrogel at concentrations of 10 mg/mL, 20 mg/mL and 25 mg/mL were manually extruded at room temperature (~22°) C. The 10 mg/mL and 20 mg/mL formulations were not capable of forming a filament upon extrusion, whereas the 25 mg/mL formulation was able to form a filament.

Evaluating the filament formation capacity of hydrogels is a simple way to study its ability to be extruded in a controlled manner, which is a useful feature for 3D bioprinting and other applications requiring the material to be delivered through a nozzle or needle. Moreover, this evaluation can be performed as an initial screening to discard hydrogel formulations unsuitable to be extruded. For this experiment, three different formulations of the methacryloyl-modified ECM hydrogel described in Example 1 were prepared and stored in 3 mL syringes coupled to 22 G conical nozzles. Then, the hydrogels were manually extruded at room temperature (~22°) C. and images at the tip of the nozzle were captured at the moment of extrusion. The collected images were qualitatively analyzed to determine drop or filament formation of the material upon deposition. Results showed that the 10 mg/mL and 20 mg/mL formulations were not capable of forming a filament upon extrusion, whereas the 25 mg/mL formulation was able to form a filament (FIG. 4).

Electroconductivity

Figure 5A:
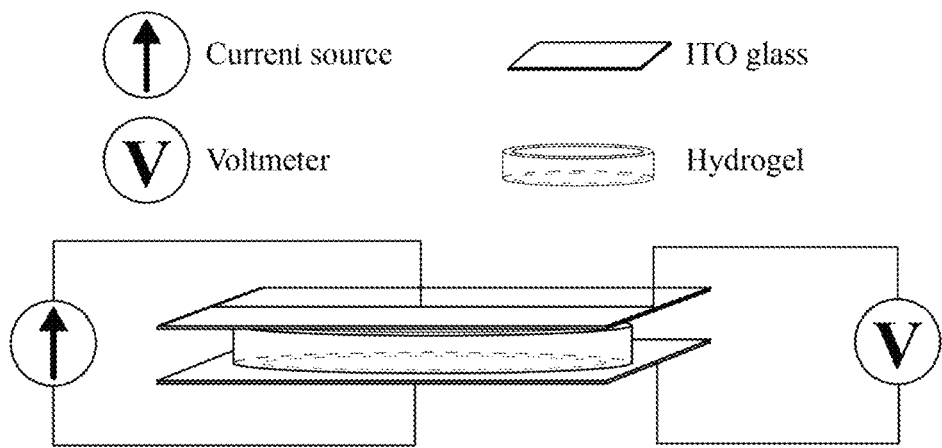
FIG. 5A Electroconductive properties—Electrical conductivity properties of the hydrogels described in Example 1 were determined by the four-point probe method using a S-302-4 Four Point Resistivity Probing Equipment (Signatone, USA) coupled with a 2450 SMU source meter (Keithley, USA) from 10 kHz to 1 Hz with an applied AC potential of 10 mV versus the reference electrode potential.
Figure 5B:
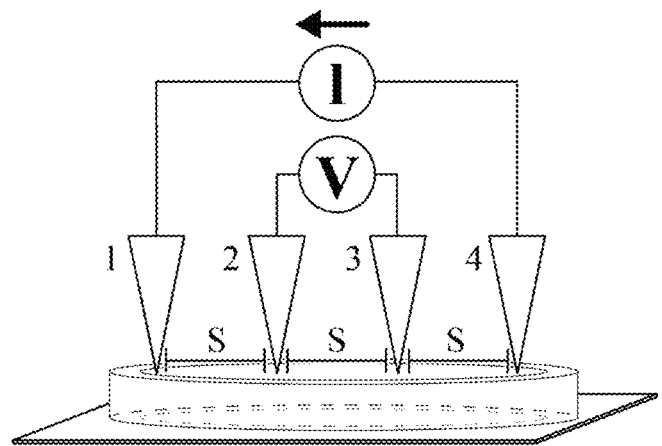
FIG. 5B Electroconductive properties—For measuring the electrical resistance of the hydrogels using a 2450 SMU source meter (Keithley, USA), the hydrogel was deposited between two indium tin oxide (ITO) glass slides that were connected to the source meter. Next, a DC current stimulus was applied, and the corresponding voltage was recorded FIG. 6A Scanning electron microscopy (SEM) image view of the methacryloyl-modified ECM hydrogel—Methacryloyl-modified ECM hydrogel after being crosslinked with temperature (at 37°) C.

Electrical conductivity properties of the hydrogels described in Example 1 were determined by the four-point probe method using a S-302-4 Four Point Resistivity Probing Equipment (Signatone, USA) coupled with a 2450 SMU source meter (Keithley, USA) from 10 kHz to 1 Hz with an applied AC potential of 10 mV versus the reference electrode potential (FIG. 5A). In addition, electrical resistance of the hydrogels was measured using a 2450 SMU source meter (Keithley, USA). For this, the hydrogel was deposited between two indium tin oxide (ITO) glass slides that were connected to the source meter (FIG. 5B). Next, a DC current stimulus was applied, and the corresponding voltage was recorded. Resistance was subsequently determined by using the Ohm's law.

Microscopical Structure

Figure 6A:
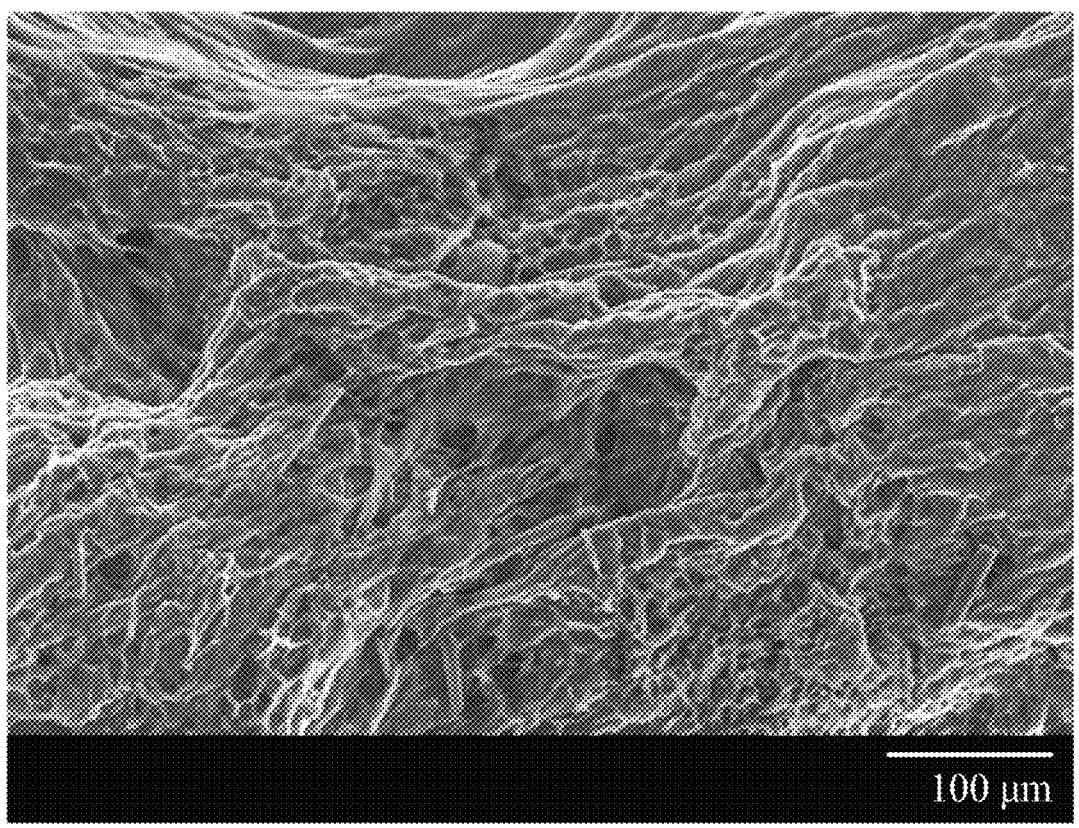
FIG. 6B Scanning electron microscopy (SEM) image view of the methacryloyl-modified ECM hydrogel—Hydrogel after irradiation with visible light (photocrosslinking).
Figure 6B:
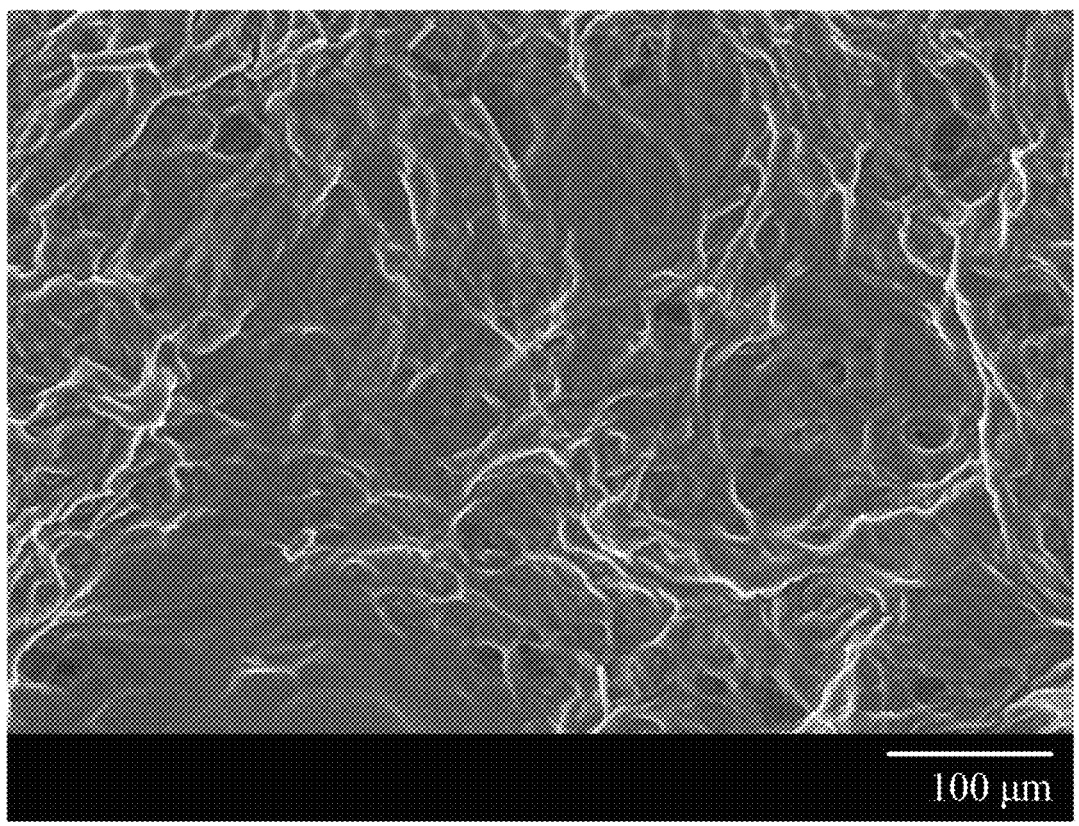

The microscopical structure of the hydrogels described in Example 1 was investigated using scanning electron microscopy (SEM). Images were collected at a 20 kV accelerating voltage with a 200× magnification. SEM images of the hydrogel described in Example 1 were obtained after crosslinking the samples solely with temperature by incubation at 37° C. for 15 min (FIG. 6A) and after crosslinking the samples solely by irradiation with blue light (FIG. 6B). After crosslinking with blue light, the hydrogel appears to be less porous and with a more dense structure, which suggests that a higher degree of crosslinking is achieved by exposing the hydrogels to visible light than by increasing its temperature to physiological conditions.

Example 4. Method for Obtaining a Hydrogel Comprising Immobilized Bioactive Molecules In order to obtain a hydrogel comprising immobilized bioactive molecules following the general procedure described in the Example 1 graphene nanoflakes were functionalized with bioactive molecules, specifically buforin II, before being incorporated into the working solution.

For functionalization, graphene oxide nanoflakes (100 mg) were suspended in 40 mL of type I water and sonicated for 1 min (frequency 40 kHz, amplitude 38%) at room temperature (~ 22°) C. Next, 1 mL of a tetramethylammonium hydroxide solution at a 25% (v/v) concentration and 50 μL of glacial acetic acid were added to the suspended graphene oxide under constant stirring (200 rpm) for 5 min at room temperature (~22°) C. Subsequently, 1 mL of a (3-aminopropyl)triethoxysilane solution at a 10% (v/v) concentration was added to the mixture and left at the same conditions (200 rpm, ~ 22° C.) for 1 h. The resulting amino-coated graphene oxide was successively washed twice with type I water to remove unreacted reagents. The next step consisted in immobilizing polyethylene glycol (PEG) on the surface of the nanoparticles, which works as a linker molecule between the surface of graphene oxide and the buforin II, which is necessary for preserving the biological activity of immobilized bioactive molecules.

For immobilizing PEG, amino-coated graphene oxide nanoflakes (100 mg) were resuspended in 40 mL of type I water and sonicated for 1 min (frequency 40 kHz, amplitude 38%) at room temperature (~22°) C. Then, 2 mL of a 2% (v/v) glutaraldehyde solution were dissolved in 5 mL of type I water and subsequently added to the solution. The resulting mixture was left under constant magnetic stirring (200 rpm) at room temperature (~22)° ° C. for 24 h. PEG-modified graphene oxide was thoroughly washed 3 times with type I water for removing unreacted reagents.

Finally, for the immobilization of buforin II, PEG-modified graphene oxide (100 mg) was resuspended in 40 mL of type I water and sonicated for 1 min (frequency 40 kHz, amplitude 38%) at room temperature (~22°) C. Separately, EDC (12.3 mg), NHS (7.4 mg) and buforin II (1 mg) were dissolved in 2 mL of dimethylformamide and subsequently added to 6 mL of type I water. The resulting mixture was left at constant magnetic stirring (200 rpm) and 37° C. for 15 min. Then, this solution was added to the PEG-modified graphene oxide solution and left at constant magnetic stirring (200 rpm) at room temperature (~22° C.) for 24 h. Buforin II-coated graphene oxide was carefully washed 3 times with type I water and stored at 4° C.

For incorporating the buforin II-coated graphene oxide into the working solution, the nanoparticles were centrifuged and concentrated on 50 mL centrifuge tubes. Next, the concentrated solution was added to the working solution described in Example 1 in order to achieve a final concentration of 0.5 mg/mL of nanoparticles on the solution. The subsequent steps to obtain a hydrogel are the same as described in Example 1.

Example 5. Method for Obtaining a Hydrogel Comprising Additional Natural Polymers Chitosan (CTS) was solubilized in a 0.17 M acetic acid solution at a 3.7 mg/mL concentration at room temperature under constant magnetic stirring for 1 h. Biochemical modification of the solubilized chitosan was performed using methacrylic acid (methacryloyl-modified chitosan), by solubilizing EDC, NHS, and the methacrylic acid in a 50% (v/v) DMF solution and the resulting mixture was heated at 40° C. for 15 min under constant stirring. This was done to activate and stabilize the carboxyl groups of methacrylic acid with the aid of EDC and NHS. After activation was completed, the mixture was added to the CTS and left to react for 24 h under constant stirring at room temperature. Next, rotary evaporation was performed to concentrate the methacryloyl-modified chitosan.

100 mL of the modified-chitosan solution were subject to rotary evaporation for 1.25 h at 70° C. and under vacuum. The final volume (approximately 10 mL) was dialyzed by loading it into a dialysis cassette and submerging it in acetic acid at a 0.17 M concentration. The volume of the acetic acid solution was 100 times the volume of methacryloyl-modified chitosan. The dialysis process was held for 48 h, time in which the acetic acid solution was replaced with a fresh solution every 4 h.

After the dialysis process was completed, the methacryloyl-modified chitosan solution was frozen at −80° ° C. for minimum 12 h and subsequently lyophilized to remove its liquid content and moisture. The obtained product was a white cloud-like 3D matrix. For obtaining a hydrogel from methacryloyl-modified chitosan and methacryloyl-modified ECM, a 0.02 M acetic acid solution was used for the solubilization of the resulting lyophilized products. For each of them, the white cloud-like 3D matrices were solubilized at twice the desired final concentration of the hydrogels. While keeping the temperature of the mixture below 10° C., the solubilized products were mixed in equal parts (1:1) with the aid of a mechanical homogenizer at 5000 rpm for 1 min. Finally, a working solution was prepared as described in Example 1 and incorporated into the hydrogel mixture at a 1:1 proportion, while keeping the temperature of the mixture below 10° C. and protecting it from light.

Example 6. Compositions of Hydrogels with Additional Natural Polymers

The following hydrogels were obtained by following the method of Example 5:

| Component | | A6 | A7 | A8 | A9 |
|---|---|---|---|---|---|
| Lyophilized biochemically-modified ECM | | 15 mg/mL | 20 mg/mL | 15 mg/mL | 25 mg/mL |
| Electroconductive nanomaterial | | 0.25 mg/mL | 0.25 mg/mL | 0.5 mg/mL | 0.25 mg/mL |
| Photoinitiator molecule | | 0.5% mg/mL | 0.5 mg/mL | 0.5 mg/mL | 0.5 mg/mL |
| Natural polymer | | 10 mg/mL | 10 mg/mL | 10 mg/mL | 5 mg/mL |
| Solvent | Acetic acid | 0.01M | 0.01M | 0.01M | 0.01M |
| | Cell culture medium | 50% v/v | 50% v/v | 50% v/v | 50% v/v |

Example 7. Characterization of Hydrogels with Additional Natural Polymers

In addition to the general physicochemical characterization of hydrogels described in Example 3, the bioadhesive potential of methacryloyl-modified chitosan of Example 5 and methacryloyl-modified ECM hydrogels of Example 1 were evaluated, as follows:

Butt Joint Test

The butt joint test seeks to evaluate how the hydrogel, when used to adhere two bovine femur bone specimens, could affect load and elongation forces supported by this hydrogel-bone specimen's complex. Specifically, 200 uL, 500 uL and 800 uL of the hydrogel described in Example 5 were applied in the cleaned cut surfaces of the bone specimens. Two specimens were pressed together and crosslinked by exposure to irradiation for 5 minutes from a blue light source (405 nm). Butt joint tests were conducted at a constant displacement rate of 0.1 mm/s in a planar uniaxial machine (Bose, Electroforce, 500 N load cell) until fracture.

Figure 7A:
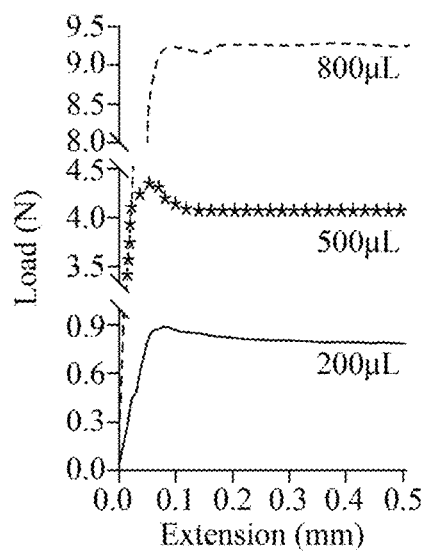
FIG. 7A Adhesive properties of methacryloyl-modified ECM hydrogel incorporated with a chitosan-based hydrogel—The load vs. elongation curve, shows that there is a direct relationship between the load and the added hydrogel content.

Results suggest that if the amount of hydrogel added on the surface of the specimens increase, the elongation force supported by the complex increases as well. Moreover, with the addition of 200 μL, the maximum elongation was 0.5 mm, while for the complex with 800 μuL this was around 5 mm. In particular, the failure in all three tests was within the crosslinked hydrogel instead of the hydrogel-bone junction, which indicates that this hydrogel has promising potential as bone bioadhesive. With the load vs. elongation curve, it was found that there is a direct relationship between the load and the added hydrogel content (FIG. 7A). A 9N load was exceeded for the specimens with the highest amount (800 uL), while those with the smallest amount (200 uL) only supported a 1 N load. Moreover, a pseudoplastic behavior is observed since a plateau is before fracture (separation) occurs.

Adhesion Test Under Wet Conditions

Figure 7B:
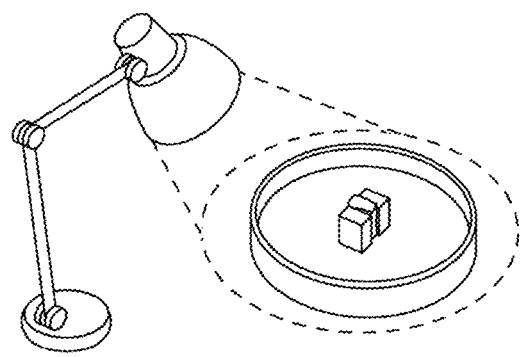
FIG. 7B Adhesive properties of methacryloyl-modified ECM hydrogel incorporated with a chitosan-based hydrogel—Two pieces of bovine femur bone were adhered together with the hydrogel and photocrosslinked.
Figure 7C:
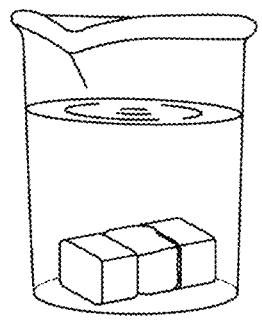
FIG. 7C Adhesive properties of methacryloyl-modified ECM hydrogel incorporated with a chitosan-based hydrogel—The hydrogel exhibits adhesive properties under wet conditions and physiological temperature (37°) C.

After exposing the hydrogel-bone specimens complex to blue light at an intensity of 1.544 mW/cm$^2$ for 10 min (FIG. 7B), the adhesive capacity of the composite hydrogel described in Example 5 under similar physiological conditions was evaluated in a proof-of-concept test. First, the irradiated complex was immersed in PBS and placed inside an incubator at 37° C. (FIG. 7C). The complex remained together under physiological conditions of temperature and constant agitation for up to two consecutive months, thus suggesting the great potential of this formulation as an extrudable bioadhesive.

Example 8. Method of Extruding Hydrogels and Hydrogels with Embedded Cells—Bioprinting Ethylene oxide (EtO) was used to sterilize the white cloud-like 3D matrices resulting from lyophilizing methacryloyl-modified ECM pregels (described in Example 1), as this method minimizes degradation of physicochemical properties while still promoting biological functions on natural materials when compared to autoclaving and filtering sterilization methods. Subsequent solubilization in 0.02 M acetic acid and incorporation of the working solution as described in Example 1 were performed.

Human foreskin fibroblasts (HFF-1, ATCC SCRC-1041) were cultured in cell culture flasks using DMEM supplemented with 10% (v/v) fetal bovine serum and 1% (v/v) penicillin-streptomycin (complete growth medium) until a cellular confluency of about 80% was achieved. Cells were detached from the culture flasks with warm trypsin at a 1× concentration, counted with the aid of a Neubauer chamber and trypan blue dye, and resuspended in 100 uL of fresh complete growth medium at a final concentration of $1.5\times10^6$ cells/mL. Cell suspension was carefully transferred to a 1 mL syringe by pipetting and gently mixed with 1 mL of the hydrogel described in Example 1 (contained in a 3 mL syringe) by adapting a female-to-female Leuer lock to the end of both syringes.

The resulting bioink (hydrogel embedded with cells for use in bioprinting) was transferred to sterile 3 mL printing amber cartridges and centrifuged at 2300 rpm for 3 min to eliminate air bubbles. Finally, these were immediately mounted on the bioprinter (BIO X, Cellink AB, Gothenburg, Sweden) printheads for subsequent bioprinting. Printing parameters were optimized for using a 25 G conical nozzle and maintaining printhead temperature below 20° C. Printbead temperature was held at 37° C. to promote thermal gelation immediately upon deposition. The minimal extrusion pressure for filament formation was found to be 15 kPa for the herein described bioink.

A CAD model of a 10 mm×10 mm×0.5 mm square was chosen for bioprinting on 6 well TC-treated plates (Corning, NY, USA). Bioprinting is illustrated in FIG. 8A.

A 405 nm photocuring module mounted on the bioprinter was used to irradiate the bioprinted constructs for 5 min, as shown on FIG. 8B. After photocrosslinking, constructs (as shown in FIG. 8C) were submerged in 4 mL of warm complete growth medium and left for incubation at 37° ° C., 5% $CO_2$ and 95% relative humidity. Culture medium was changed every two days.

Example 9. Characterization of Bioprinted Constructs

Figure 9:
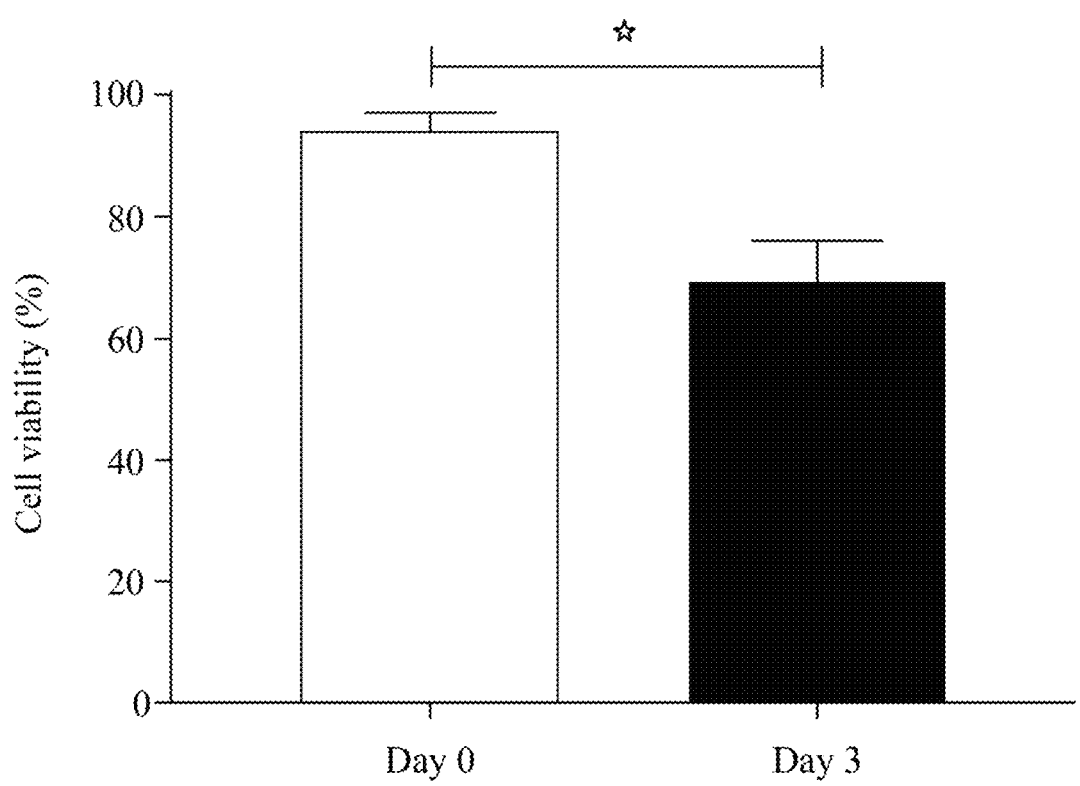

Viability of human adipose-derived mesenchymal stem cells (hAD-MSCs) embedded in the bioprinted constructs, fabricated using the hydrogel described in Example 1 and the extrusion process described in Example 8, was assessed with fluorescent stainings. Nuclei and dead cell staining was performed with bisbenzimide and propidium iodide fluorescent dyes, respectively, 2 h and 72 h after bioprinting. Accordingly, a working solution of bisbenzimide and propidium iodide fluorophores was prepared at a 1:1000 proportion with a 1× phosphate-buffered saline (PBS) each, and was added to the DMEM culture medium at a 1:4 proportion. After 45 min, all the medium was removed, the construct was fixed with 4% (v/v) paraformaldehyde for 5 min and stored in 1×PBS until subsequent analyses. A 358 nm laser excitation was performed with an Olympus FV1000 Confocal Microscope to obtain nuclei location with the emission spectrum from bisbenzimide, as well as a 559 nm laser excitation to locate dead cells within the construct due to the propidium iodide emission spectrum. Emission channels were overlapped to identify live and dead cells, where live cells comprised locations with only nuclei staining and dead cells comprised locations with overlapped nuclei and propidium iodide staining. A slight drop in cell viability was observed after 72 h of incubation (FIG. 9), but an overall adequate viability was obtained.

Those skilled in the art will recognize, or be able to ascertain using no more than routine experimentation, many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for preparing an extrudable photocrosslinkable hydrogel comprising:
   biochemically modifying an extracellular matrix (ECM) pregel;
   treating the modified ECM pregel with a working solution comprising a photoinitiator and an electroconductive nanomaterial, wherein the ECM is isolated from tissues selected from liver, urinary bladder, intestine, heart, lung, kidney, placenta, skin, omentum, cartilage, and mixtures thereof.

2. The method of claim 1, wherein the biochemically modifying step comprises:
   adding chemical groups to the ECM pregel, wherein the chemical groups are selected from methacrylate, acrylate, divinyl sulfone, thiol, and mixtures thereof;
   dialyzing and lyophilizing until obtaining a modified ECM pregel.

3. The method of claim 1, wherein the treating the modified ECM pregel comprises:
   solubilizing the biochemically modified ECM pregel and incorporating a working solution at a 1:1 ratio at 2-8° C., protected from light.

4. The method of claim 1, wherein the working solution comprises:
   DMEM cell culture medium supplemented with fetal bovine serum;
   a photoinitiator at a concentration between about 0.1 and 5% mg/ml;
   an electroconductive nanomaterial between about 0.1 and 1 mg/mL; and
   optionally, a pH regulator.

5. The method of claim 1, wherein the electroconductive nanomaterial has bioactive molecules superficially immobilized at molar ratios between 1:1 to 20:1 bioactive molecules: electroconductive nanomaterial.

6. The method of claim 5, wherein the bioactive molecules are immobilized by amine-amine or carboxyl-amine crosslinkers selected from EDC, NHS glutaraldehyde, and mixtures thereof.

* * * * *